United States Patent
Matthews et al.

(10) Patent No.: US 8,502,138 B2
(45) Date of Patent: Aug. 6, 2013

(54) INTEGRATED ION MOBILITY SPECTROMETER

(75) Inventors: Sinead Marie Matthews, Oxfordshire (GB); Lesley Anne Parry-Jones, Courtenay (GB); Allan Evans, Oxford (GB)

(73) Assignee: Sharp Kabushiki Kaisha, Osaka (JP)

( * ) Notice: Subject to any disclaimer, the term of this patent is extended or adjusted under 35 U.S.C. 154(b) by 3 days.

(21) Appl. No.: 13/194,137

(22) Filed: Jul. 29, 2011

(65) Prior Publication Data
US 2013/0026357 A1 Jan. 31, 2013

(51) Int. Cl.
*H01J 49/04* (2006.01)
*H01J 49/28* (2006.01)

(52) U.S. Cl.
USPC .................. 250/286; 250/282; 250/294

(58) Field of Classification Search
USPC ............ 250/281, 282, 287, 294, 286, 87
See application file for complete search history.

(56) References Cited

U.S. PATENT DOCUMENTS

| | | | |
|---|---|---|---|
| 3,812,355 A | 5/1974 | Wernlund et al. | |
| 5,455,417 A | 10/1995 | Sacristan | |
| 5,965,882 A | 10/1999 | Megerle et al. | |
| 6,365,901 B1 * | 4/2002 | Orr et al. | 250/380 |
| 6,495,823 B1 * | 12/2002 | Miller et al. | 250/286 |
| 6,512,224 B1 | 1/2003 | Miller et al. | |
| 6,630,663 B2 | 10/2003 | Murphy et al. | |
| 6,774,360 B2 * | 8/2004 | Guevremont et al. | 250/288 |
| 6,815,669 B1 | 11/2004 | Miller et al. | |
| 7,098,449 B1 | 8/2006 | Miller et al. | |
| 7,122,794 B1 | 10/2006 | Miller et al. | |
| 7,244,931 B2 * | 7/2007 | Zimmermann et al. | 250/292 |
| 7,813,102 B2 * | 10/2010 | Gefter et al. | 361/213 |
| 2001/0030285 A1 | 10/2001 | Miller et al. | |
| 2003/0052263 A1 | 3/2003 | Kaufman et al. | |
| 2003/0132380 A1 | 7/2003 | Miller et al. | |

(Continued)

FOREIGN PATENT DOCUMENTS

| | | |
|---|---|---|
| JP | 2004-528685 A | 9/2004 |
| JP | 2008-508693 A | 3/2008 |
| JP | 2011-077054 A | 4/2011 |
| JP | 2011-517025 A | 5/2011 |

OTHER PUBLICATIONS

International Search Report for corresponding International Patent Application No. PCT/JP2012/068042 dated Oct. 16, 2012.

*Primary Examiner* — Robert Kim
*Assistant Examiner* — David E Smith
(74) *Attorney, Agent, or Firm* — Renner, Otto, Boisselle & Sklar, LLP

(57) ABSTRACT

An ion mobility spectrometer includes a plurality of substrates defining a measurement region for receiving a singular laminar gas flow without any carrier or sheath gas. The measurement region includes an ionization region that is continuous with a detection region. An ionizing electrode, which may include a plurality of asymmetric electrodes, produces ions in the gas sample within the ionization region. The ionizing electrode may apply a time varying voltage to the gas sample to generate a time dependent ion production. A field generating electrode generates an electric field to deflect the ions in the gas sample, and a detection electrode array detects the deflected ions within the detection region. A controller is configured to determine ion species based on the detection of ions by the detection electrode array. The detection electrode array may include a plurality of detection electrodes, and the controller may be configured to differentiate ion species based on which ions are detected by which one of the detection electrodes.

21 Claims, 6 Drawing Sheets

U.S. PATENT DOCUMENTS

| | | |
|---|---|---|
| 2003/0146377 A1 | 8/2003 | Miller et al. |
| 2004/0079879 A1 | 4/2004 | Ross et al. |
| 2004/0094704 A1 | 5/2004 | Miller et al. |
| 2004/0124350 A1 | 7/2004 | Miller et al. |
| 2004/0240843 A1 | 12/2004 | Miller et al. |
| 2005/0017163 A1 | 1/2005 | Miller et al. |
| 2005/0023457 A1 | 2/2005 | Miller et al. |
| 2005/0029443 A1 | 2/2005 | Miller et al. |
| 2005/0029449 A1 | 2/2005 | Miller et al. |
| 2005/0040330 A1 | 2/2005 | Kaufman et al. |
| 2005/0051719 A1 | 3/2005 | Miller et al. |
| 2005/0133716 A1 | 6/2005 | Miller et al. |
| 2005/0139762 A1 | 6/2005 | Miller et al. |
| 2005/0145789 A1 | 7/2005 | Miller et al. |
| 2005/0156107 A1* | 7/2005 | Miller et al. .......... 250/293 |
| 2005/0173629 A1 | 8/2005 | Miller et al. |
| 2005/0230616 A1* | 10/2005 | Cameron et al. .......... 250/287 |
| 2005/0253061 A1 | 11/2005 | Cameron et al. |
| 2005/0263699 A1 | 12/2005 | Miller et al. |
| 2006/0054804 A1 | 3/2006 | Wexler |
| 2006/0060768 A1 | 3/2006 | Kaufman et al. |
| 2006/0071163 A1* | 4/2006 | Gorbunov .......... 250/292 |
| 2006/0118717 A1 | 6/2006 | Miller et al. |
| 2006/0151687 A1 | 7/2006 | Miller et al. |
| 2006/0192102 A1 | 8/2006 | Miller et al. |
| 2006/0237642 A1 | 10/2006 | Miller et al. |
| 2006/0255255 A1 | 11/2006 | Miller et al. |
| 2007/0029477 A1 | 2/2007 | Miller et al. |
| 2007/0045530 A1 | 3/2007 | Miller et al. |
| 2007/0084999 A1 | 4/2007 | Miller et al. |
| 2007/0176092 A1 | 8/2007 | Miller et al. |
| 2007/0228269 A1 | 10/2007 | Miller et al. |
| 2007/0252082 A1 | 11/2007 | Miller et al. |
| 2008/0054174 A1* | 3/2008 | Boyle et al. .......... 250/286 |
| 2008/0121794 A1 | 5/2008 | Miller et al. |
| 2008/0128609 A1 | 6/2008 | Miller et al. |
| 2008/0128612 A1* | 6/2008 | Miller et al. .......... 250/286 |
| 2008/0135745 A1 | 6/2008 | Miller et al. |
| 2008/0149823 A1* | 6/2008 | Anttalainen .......... 250/282 |
| 2008/0156981 A1* | 7/2008 | Miller et al. .......... 250/287 |
| 2008/0185512 A1 | 8/2008 | Miller et al. |
| 2008/0191132 A1 | 8/2008 | Boyle et al. |
| 2008/0224032 A1 | 9/2008 | Miller et al. |
| 2009/0189064 A1 | 7/2009 | Miller et al. |
| 2011/0006196 A1 | 1/2011 | Boyle et al. |
| 2011/0006199 A1 | 1/2011 | Mattila et al. |
| 2011/0056371 A1 | 3/2011 | Koehl |
| 2012/0025070 A1 | 2/2012 | Miller et al. |

\* cited by examiner

INTEGRATED ION MOBILITY SPECTROMETER

TECHNICAL FIELD

This invention relates to a system and methods for the quantitative analysis of the chemical composition of gaseous samples using an ion mobility spectrometry (IMS). More specifically, this invention describes an IMS device with a simplified geometry which enables a single sample gas flow without an accompanying carrier or sheath gas, and time dependent ion production and detection.

BACKGROUND ART

An ion mobility spectrometer (IMS) detects chemical species in the air by ionizing them and then applying an electric field so that speed of drift caused by the electric field can be measured. Commercial IMS devices are used, for example, to detect explosive and drug residues in security applications.

A conventional ion mobility spectrometer is depicted in FIG. 1(a). As seen in FIG. 1(a), a plasma chromatograph (IMS) chamber 150 includes an envelope 152 of electrodes containing a pair of spaced electrodes 154 and 156. A sample gas may be provided through the inlet 158 and passes through the chamber to the outlet 160. An ionizer 161 is provided adjacent the electrode 154, such that the sample gas passes the ionizer. An electric drift field is established between the electrodes 154 and 156, and a non-reactive drift gas is provided via the drift gas inlet 162. The drift gas fills the region of the chamber between a pair of shutter grids 164 and 166 typically formed as grids of wires in which each alternating wire is held at equal and opposite potentials. The first shutter grid 164 has a mixed ion species population, represented by the letters A, B, and C in FIG. 1(a). The various ion species become segregated in the drift region, and collected at the electrode 156 from which the various ion species may be determined. A conventional IMS device as depicted in FIG. 1(a) is exemplified by the device disclosed in Wernlund, et al., U.S. Pat. No. 3,812,355 issued on May 21, 1974.

In such devices, an air sample is ionized (usually by radioactivity or an electric discharge), and ions are then accelerated towards a detector plate by an electric field applied parallel to the sample gas flow. The current at the detector plate is measured as a function of time. Ions with high mobility (that is high speed when pushed by an electric field) arrive first, while low mobility ions arrive later. Ionic mobility varies non-linearly in high electric fields; therefore, methods have been developed to improve an IMS' ability to identify different chemical species by using a range of different applied electric field strengths.

Design of this type of IMS device is difficult and involves various compromises. For example, the gas typically must be confined during ionization. Otherwise, the gas spreads in the drift direction and accurate measurements of mobility cannot be made. This makes high concentrations of ions difficult to manage and limits the sensitivity of the instrument. The transfer of ions from the ionization chamber into the drift tube is difficult to control. Miniaturizing this design would improve ion losses and create more uniform electric fields, but it would also reduce the resolution as the separation of ions is proportional to the time they spend in the drift tube.

To overcome the problems of miniaturization, an alternative design using an electric field applied transverse to the gas flow has been developed. This type of device is exemplified by the device depicted in FIG. 1(b). As depicted in FIG. 1(b), a gas possibly having an ionized species may enter a measurement region 108 of a flow channel 102 having a channel wall 104. An electric field indicated by the arrow 110 is generated by a source 106. The source 106 may include a plurality of counter electrodes 112 having a voltage applied by a power supply 114. A sensor electrode 118 may be formed of a group 122 of sensor elements 120. Such a device is comparable to the devices disclosed in Murphy et al., U.S. Pat. No. 6,630,663 issued on Oct. 7, 2003, Sacristan, U.S. Pat. No. 5,455,417 issued on Oct. 3, 1995, and Megerle et al., U.S. Pat. No. 5,965,882, issued on Oct. 12, 1999. In such devices, rather than accelerate the ions towards the detector at the end of the drift region, the ions are directed onto the sensor elements of the sensor electrode by a combination of air flow and electric field driven motion. These designs still use a separate ionization chamber and drift region.

If the ions enter the drift region in a zone which is short in the direction parallel to the field, then the mobility of ions can be measured precisely. Such a system is depicted in FIG. 2. As depicted in FIG. 2, an IMS 212 includes an ionizer 204 and a linear electrometer array 210. A gas sample 202 flows through the ionizer 204, which injects the ionized gas sample in the chamber of the IMS 212. A laminar, non-ionized gas flow 206, also referred to in the art as a sheath air, is injected into the IMS which acts as a carrier gas. The laminar gas flow 206 causes larger ions to move faster than smaller ions, and a generated electric field 208 directs ions towards the array 210. The combined effects of the electric field 208 and laminar gas flow 206 causes different ion species to be directed to the array at different points, which permits differentiation of the ion species. A device of this type is exemplified by the device disclosed in Wexler, US 2006/0054804 published on May 16, 2006.

In this manner, precise measurements of the mobility of ions can be achieved using a sheath (or carrier) gas (See also Zhang et al., Int. J. Mass Spec. 258 (2006) at pp. 13-20; Zimmermann et al., Act. B 125 (2007) at pp. 428-434.) In such a configuration, however, the flow rates of the sample and sheath air streams must be balanced. A significant disadvantage of this method is that only a small proportion of the air entering the drift region is ionized, reducing the total detection current and the signal to noise ratio.

Other methods for improving the resolution in a miniaturized device have also been developed. In Field Asymmetric Ion Mobility Spectrometry (FAIMS), detector electrode(s) are placed at the end of the drift tube, and a high frequency alternating electric field is applied within the drift tube. The applied electric field will divert most ions into the channel walls, and only ions of a specific mobility will not be diverted by this field and will reach the detector electrode(s). Such a device is depicted in FIG. 1(c). The FAIMS ion separator of FIG. 1(c) includes an analyzer region 144 defined by two parallel electric plates 138 and 140. A voltage source 136 provides an asymmetric waveform to generate an electric field between the plates. Accordingly, when an ion 132 enters the analyzer region 144 via a gas stream 134, the ion will travel in an exemplary ion pathway 142. As stated above, the ions will tend to be diverted into the walls of the analyzer region and detected. While such systems can be miniaturized and included in an array, only a single ion mobility can be detected at a given time, and the technique is more sensitive to environmental influences. This type of device is exemplified by the devices disclosed in Guevremont et al., U.S. Pat. No. 6,774,360 issued on Aug. 10, 2004, and Zimmermann et al., U.S. Pat. No. 7,244,931 issued on Jul. 17, 2007.

SUMMARY OF INVENTION

The object of this invention is to provide an enhanced system and methods of ion mobility spectrometry to achieve effective chemical resolution and sensitivity without the need for carrier gases or radioactive elements.

The described invention includes an IMS device in which a single laminar air stream is ionized by electric discharge in a continuous flow, upstream, but not separate from, the drift region. The non-ionized sample stream then behaves as a sheath gas, to control the ion pathways as they enter the drift region. An electric field is applied, either
  i) transverse to the air flow, to deflect the ions towards a detector electrode array positioned on the bottom wall of the drift region, or
  ii) parallel to the air flow to accelerate the ions towards a detector electrode at the end of the drift region As the ion production may be varied with time, frequency analysis or lock-in techniques can be applied at the detector electrodes to reduce background electrical noise.

The advantages of the described design include:
Reduced ion losses: as there is no separate ionization chamber and the distance between ion source and drift region is minimized, most of the ions generated will be detected. As the position of ion generation is accurately known, the accuracy of the ion mobility measurement is improved.
Single sample air stream: the well defined ion pathway created by the position of the ion source and the laminar flow of air past the ion source means that a second air stream (sheath air) is not required.
Improved sensitivity: the combination of electrical ionization methods, well defined air flow pattern, and minimized distance between ion generation and detection enables the use of time varying ion production mechanisms and detection strategies using these time varying mechanisms to remove noise from the measured signal.

Accordingly, an aspect of the invention is an ion mobility spectrometer (IMS). An exemplary embodiment of the IMS includes a plurality of substrates defining a measurement region for receiving a singular laminar gas sample flow, wherein the measurement region comprises an ionization region that is continuous with a detection region. An ionizing electrode produces ions in the gas sample within the ionization region. A field generating electrode generates an electric field to deflect the ions in the gas sample, and a detection electrode array detects the deflected ions within the detection region. A controller configured to determine ion species based on the detection of ions by the detection electrode array.

In another exemplary embodiment of the IMS, the detection electrode array includes a plurality of detection electrodes, and the controller is configured to differentiate ion species based on which ions are detected by which one of the detection electrodes.

In another exemplary embodiment of the IMS, the ion mobility spectrometer the ionizing electrode includes plurality of asymmetric electrodes.

In another exemplary embodiment of the IMS, the plurality of asymmetric electrodes includes a first asymmetric electrode positioned on a first of the plurality of substrates, and a second asymmetric electrode positioned on a second of the plurality of substrates.

In another exemplary embodiment of the IMS, the plurality of asymmetric electrodes includes a first asymmetric electrode positioned on one of the plurality of substrates outside the measurement region, and a second asymmetric electrode positioned on the one of the plurality of substrates within the measurement region.

In another exemplary embodiment of the IMS, the field generating electrode produces an electric field that has a voltage polarity opposite to that of the ionizing electrode.

In another exemplary embodiment of the IMS, the measurement region comprises an ionization region in which the gas sample is ionized by the ionizing electrode, and a detection region containing the detection electrode array.

In another exemplary embodiment of the IMS, the IMS includes at least three substrates defining a plurality of measurement regions, wherein each measurement region receives a singular laminar gas sample flow.

In another exemplary embodiment of the IMS, a middle substrate of the three substrates includes a plurality of ionizing electrodes positioned on opposite sides of the middle substrate such that an ionizing electrode is positioned within each measurement region.

In another exemplary embodiment of the IMS, outer substrates of the three substrates each include a detection electrode array for detecting the deflected ions.

Another aspect of the invention is a method of determining ion species with an ion mobility spectrometer. The method may include the steps of providing a singular laminar gas sample flow; defining a measurement region for receiving the singular laminar gas sample flow, wherein the measurement region comprises an ionization region that is continuous with a detection region; ionizing the gas sample to produce ions in the gas sample within the ionization region; generating an electric field within the detection region to deflect the ions in the gas sample; detecting the deflected ions within the detection region with a detection electrode ray; and determining ion species based on the detection of ions by the detection electrode array.

In another exemplary embodiment of the method of determining ion species, the detection electrode array includes a plurality of detection electrodes, and determining the ion species includes differentiating ion species based which ions are detected by which one of the detection electrodes.

In another exemplary embodiment of the method of determining ion species, ionizing the gas sample includes applying a time varying voltage to the gas sample to generate a time dependent ion production.

In another exemplary embodiment of the method of determining ion species, the applied ionizing voltage oscillates around an ionization threshold voltage at which chemical species in the air sample tend to ionize to generate an ion production switching on and off at a frequency of the oscillations.

In another exemplary embodiment of the method of determining ion species, determining the ion species further includes performing a frequency analysis of the currents at the detector electrode array.

In another exemplary embodiment of the method of determining ion species, the ionization voltage is modulated at two frequencies including a first frequency having a voltage above the ionization voltage during which ions are produce, and a second frequency to provide a separation period during which ions are not produced.

In another exemplary embodiment of the method of determining ion species, ionizing the gas sample includes applying a time varying voltage that is switched between a negative and positive polarity.

In another exemplary embodiment of the method of determining ion species, generating an electric field within the detection electrode includes applying a time varying electric field in the detection region.

Another aspect of the invention is a gas analysis system including a pump for pumping a singular laminar gas sample, and the described ion mobility spectrometer, wherein the IMS receives the gas sample from the pump.

In another exemplary embodiment of the gas analysis system, the gas analysis system further includes a humidity controller for controlling the humidity of the gas sample; an ion trap for removing ions that are preexisting in the gas sample before the gas sample enters the ion mobility spectrometer; and a filter for removing particulates from the gas sample.

In another exemplary embodiment of the gas analysis system, the gas analysis system further includes a heating element for heating a solid or liquid material to produce the gas sample.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

In the annexed drawings, like references indicate like parts or features.

DESCRIPTION OF REFERENCE NUMERALS

Figure 1A:
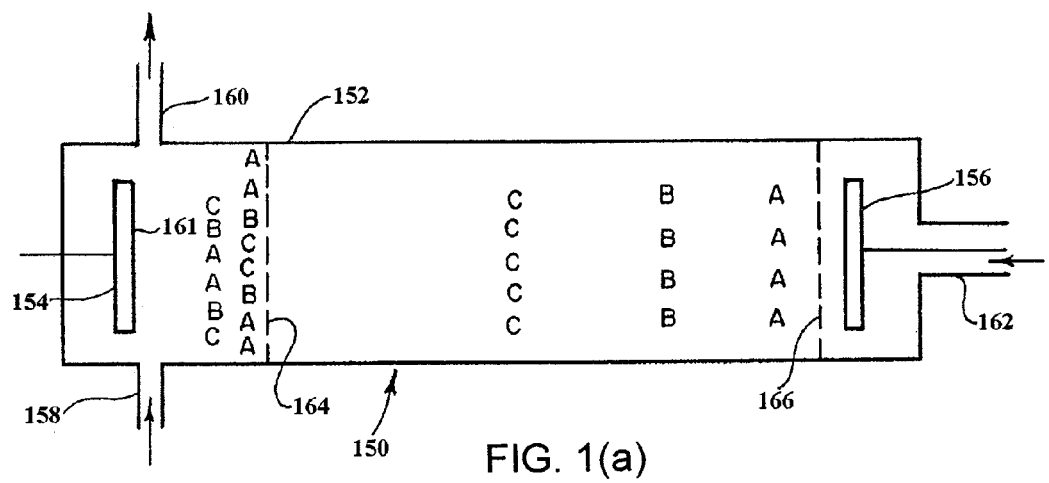
FIG. 1(a) is a schematic diagram depicting a conventional ion mobility spectrometer.
Figure 1B:
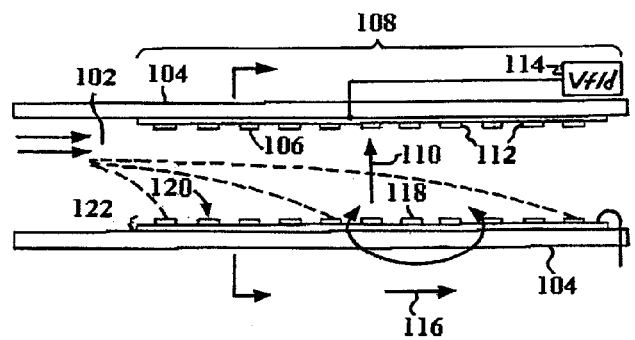
FIG. 1(b) is a schematic diagram depicting a conventional cross-flow ion mobility spectrometer.
Figure 1C:
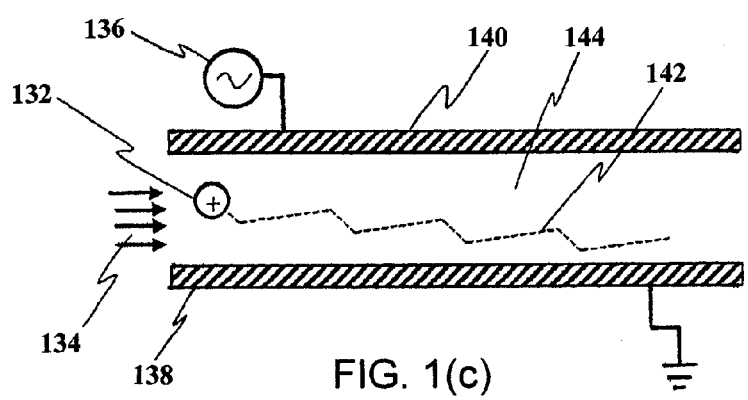
FIG. 1(c) is a schematic diagram depicting a conventional field asymmetric ion mobility spectrometer.
Figure 2:
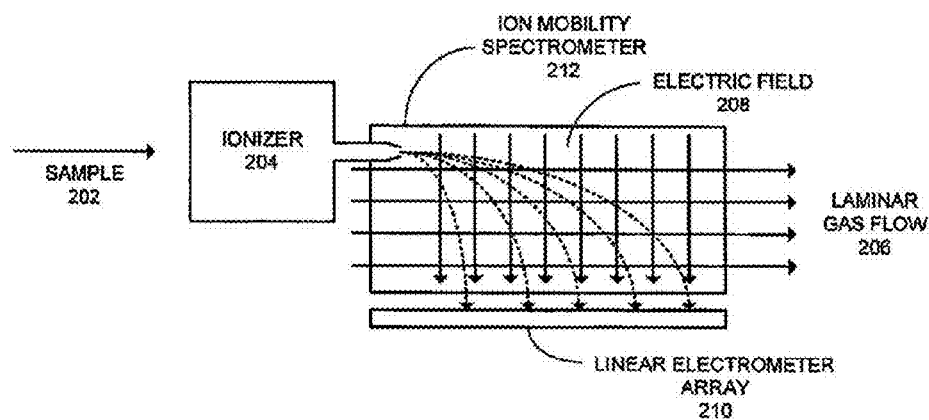
FIG. 2 is a schematic diagram depicting a conventional controlling of an ion trajectory in a miniaturized device using sheath gas flow.

102: Channel
104: Channel wall
106: Source of electric field
108: Measurement region
110: Electric field
112: Counter electrode
114: Power supply
116: Direction of air flow
118: Sensor electrode
120: Sensor element
122: Group of sensor electrodes
132: Ion
134: Gas stream
136: Voltage source
138: Parallel plate
140: Parallel plate
142: Ion pathway
144: Analyzer region
150: Plasma chromatograph (IMS) chamber
152: Envelope of electrodes
154: Electrode for creating electric field (1 of a pair)
156: Electrode for creating electric field (1 of a pair)
158: Sample gas inlet
160: Outlet
161: Ionizer
162: Non-reactive (drift) gas inlet
164: Shutter grids (1 of pair)
166: Shutter grids (1 of pair)
202: Sample gas flow
204: Ionizer
206: Laminar gas flow (sheath air)
208: Applied electric field
210: Linear electrometer array
212: Ion mobility spectrometer
300: Laminar sample air flow
301: Ionizing electrode
302: Asymmetric electrodes for ion production
303: Detector electrode array
304: Detector electrodes
305: Measurement region
306: Electrode to apply electric field
308: Glass wafer
310: Entrance region
312: High mobility ion
314: High mobility ion pathway
316: Low mobility ion
318: Low mobility ion pathway
320: Ionization region
321: Detection region
322: Controller
350: Ion mobility spectrometer
502: Asymmetric electrodes—ion tip
504: Asymmetric electrodes—counter electrodes
602: Asymmetric electrodes—ion tip
604: Asymmetric electrodes—counter electrodes
606: Wafer made of dielectric material of suitable thickness to obtain electrical discharge
700: Ion production threshold value
702: Ion production pulse
704: Time period between ion pulses
800: Split laminar air flow
802: Detector electrodes
803: Additional detector electrode array
804: Asymmetric electrode—ion tip
805 Measurement regions
806: Asymmetric electrode—$2^{nd}$ ion tip
900: Air pump
902: Humidity controller
904: Ion trap 906: Particulate sizer/counter
908: Ion mobility spectrometer
910: Detector electronics
912: Controlling microprocessor
914 Heating element
950: Gas analysis system

DETAILED DESCRIPTION OF INVENTION

Figure 3:
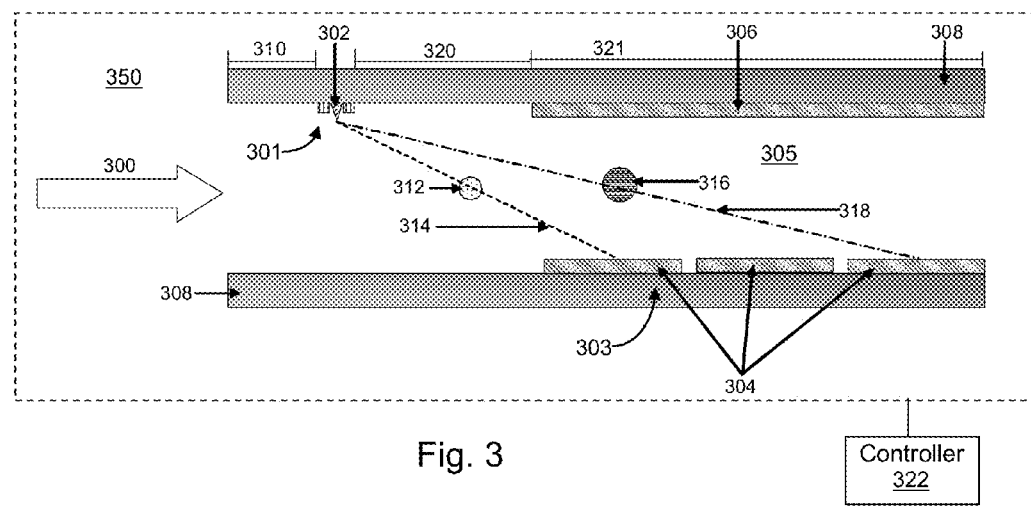
FIG. 3 is a schematic diagram depicting a cross section of an ion mobility spectrometer in accordance with embodiments of the present invention, illustrating well defined ion pathways created by the combination of laminar air flow and applied electric field.

A schematic diagram depicting a first embodiment of the present invention is shown in FIG. 3. FIG. 3 depicts an ion mobility spectrometer (IMS) 350 that includes two glass wafers 308 which constitute a plurality of substrates that define a measurement region 305 for receiving a singular, laminar gas sample flow. The IMS may include an ionizing electrode 301 including asymmetric electrodes for ion production 302, and a detector electrode array 303 that includes a plurality of detector electrodes 304.

During a measurement, a single stream of particulate free, non-ionized sample air 300 is pumped into an entrance region 310. The entrance region is of sufficient length to ensure that the air flow is laminar prior to reaching the asymmetric electrodes 302. A negative high voltage is applied between the asymmetric electrodes to produce a negative electrical discharge. This ionizes the air sample by secondary reactions between the ions directly ionized by the electrical discharge and other chemical components of the sample. This ionization mechanism produces only a small volume of ionized air close to the top substrate of the substrates 308. The rest of the air sample remains non-ionized and has a comparable function as a sheath or drift gas as described above.

The measurement region 305 comprises an ionization region 320, in which portions of the gas sample are ionized as described above, and a detection region 321. The ionization region 320 is continuous with the detection region 321 in the sense that there is no physical separation or barriers between the ionization region 320 and detection region 321. This configuration is in contrast to conventional configurations, in which an ionization chamber or region is provided separate from the detection region. With a configuration having a measurement region including continuous ionization and detection regions, the gas sample may be provided as a singular, laminar flow of gas through the entire measurement region 305 without the need for providing an additional carrier or sheath gas. In other words, in the single gas sample flow, the non-ionized gas portions act as a carrier for the ionized gas portions. To ensure that all of the secondary reactions by which chemical species in the air sample are ionized can be completed prior to entering the detection region, the distance of the ionization region 320 from the ionization electrode to the detection region 321 is preferably one half or less of the distance of the measuring region. The distance of the ionization region 320 will be dependent on a number of experimental parameters including, for example, air velocity, humidity, and temperature.

The portion of the measurement region 305 that is outside of the ionization region forms the detection region 321 that includes the detection electrode array. In the detection region 321 of the measurement region 305, a positive electric field is applied perpendicular to the air flow between the detector electrodes 304 and the field generating electrode 306. The positive electric field, therefore, is of an opposite voltage polarity as compared to the ionizing electrode, and thus deflects the negative ions towards the detector electrode array 303 including the plurality of detector electrodes 304. The combination of the laminar gas flow and applied electric field acts to spatially separate the ions according to their mobility along the detector electrode array. Typically, the high mobility ions 312 are deflected more than low mobility ions 316, resulting in their detection at electrodes closer to the entrance of the IMS. As seen in FIG. 3, for example, ion 312 may deflect along an ion pathway 314, and ion 316 may deflect along an ion pathway 318, such that the ion 312 is detected by an electrode 304 that is closer to the IMS entrance region 310 as compared to the electrode 304 that detects ion 316.

The size of the ionic current detected at each electrode array element is correlated to the concentration of a given ionic species in the air sample, and consequently the concentration of all the chemical species in the air sample can be determined. For example, the IMS may include a controller 322 configured to determine ion species based on the detection of ions by the detection electrode array. In particular, because the detection electrode array includes a plurality of detection electrodes, the controller may be configured to differentiate ion species by which ions are detected by which one of the detection electrodes. The controller 322 may be provided in the form of a control circuit or processing device that may execute program code stored on a machine-readable medium. Such controller functionality could also be carried out via dedicated hardware, firmware, software, or combinations thereof, without departing from the scope of the invention.

As is known in the art, the applied electric field in the detection region may be varied so as to exploit the non-linear response of the ionic mobility and create a unique fingerprint for each chemical species.

In another exemplary embodiment of the invention, a time varying voltage is applied to the ionizing electrode 301 (asymmetric electrodes 302) such that a time varying electric field is applied to the gas sample to generate a time dependent ion production. In exemplary embodiments including a time varying voltage, the applied voltage of the ionizing electrode oscillates around an ionization threshold voltage at which chemical species in the air sample tend to ionize, resulting in ion production switching on and off at the applied frequency. In this scenario, ions are generated and flow into the detection region 321 in pulses. In this embodiment, the controller 322 may perform a frequency analysis of the currents at the detector electrode array electrodes, which enables the isolation of the current due to the ion pulses and the removal of currents detected at extraneous frequencies. There may also be phase differences between the applied waveform of the time varying high voltage, and the detected waveform of the ion current detection electrodes. These phase differences that may arise as a result of the ionization mechanism also may be used to target a specific ion signal and enhance the current signal to noise ratio.

Figure 4:
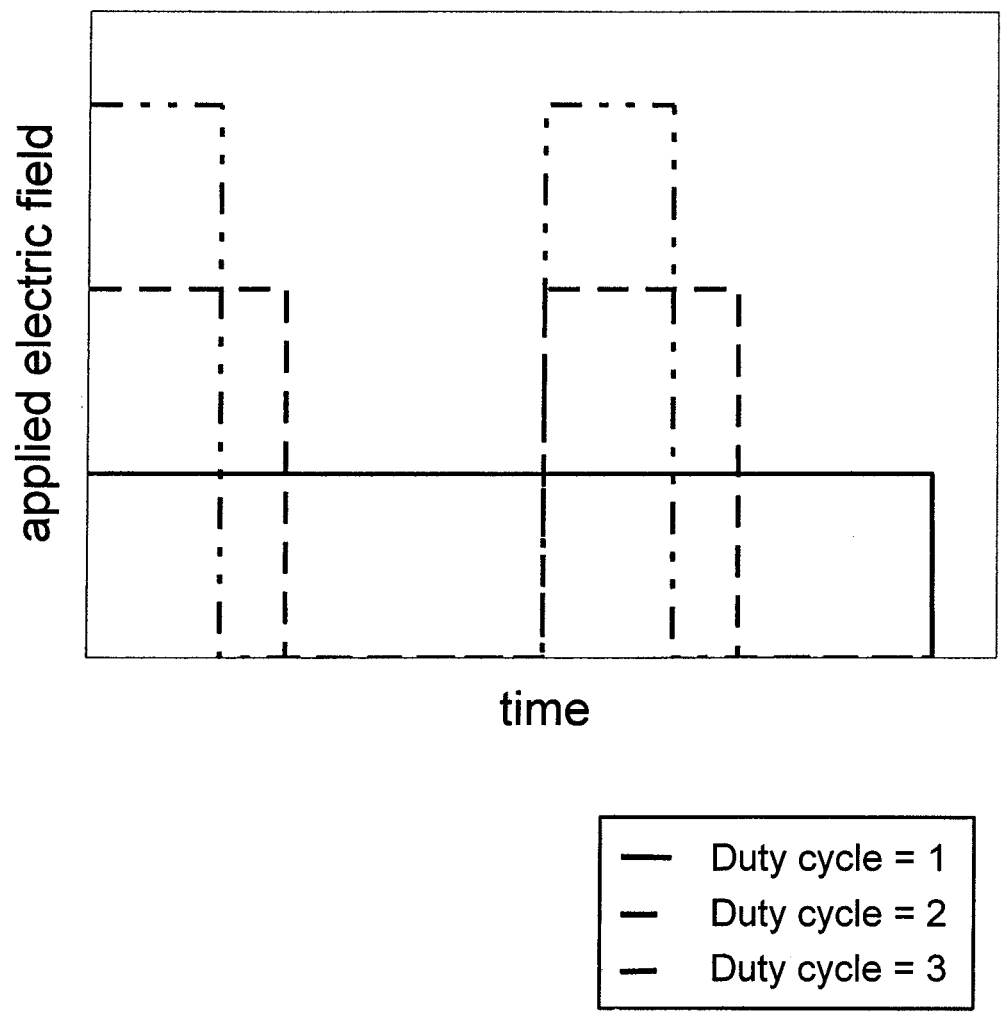
FIG. 4 is a graphical illustration of different duty cycles for the applied electric field in the detector region in accordance with embodiments of the present invention.

In another exemplary embodiment of the invention, the field generating electrode 306 may apply a time varying electric field in the detection region 321 of the measurement region 305. By varying the duty cycle of the applied field, a high field can be used for a shorter period. For example, FIG. 4 depicts a field strength three times stronger is applied for one-third of the time period. This results in an average velocity of an ion within the drift region being of the same order, regardless of whether a high or low field is applied. Utilizing a time varying electric field has an advantage that the same experimental parameters (e.g., geometry, flow speed etc.) can be used for both high and low field measurements.

In another exemplary embodiment of the invention, the time varying voltage applied to the asymmetric electrodes 302 may be such that ion production is switched between a negative and a positive polarity. As is understood by those of ordinary skill in the art, changing the polarity of the discharge provides another mechanism of distinguishing between chemical species, thereby improving the resolution of the described invention.

In another exemplary embodiment of the invention, the polarity of the applied electric field between electrodes 304 and 306 is reversed so as to deflect positive ions onto the detector electrodes 304. This electric field reversal does not necessarily have to coincide with inverting the polarity of the electrical discharge.

Figure 5:
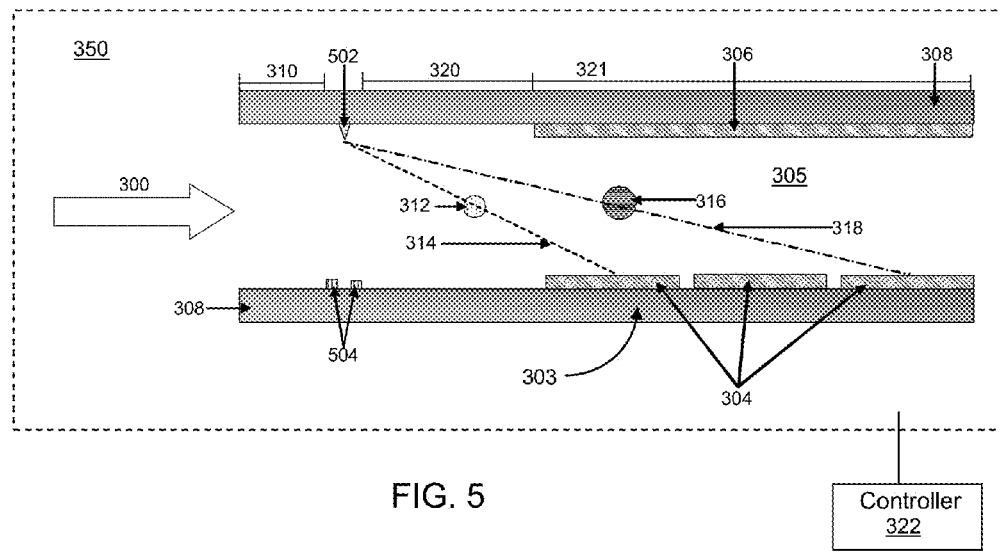
FIG. 5 is a schematic diagram depicting an IMS device with asymmetric ion production electrodes on the top and bottom substrate wafers, in accordance with embodiments of the present invention.

FIG. 5 depicts another exemplary embodiment of the ion mobility spectrometer (IMS) 350. In the embodiment of FIG. 5, the plurality of asymmetric electrodes may include a first asymmetric electrode positioned on a first of the plurality of substrates and a second asymmetric electrode positioned on a second of the plurality of substrates. For example, as depicted in FIG. 5, the asymmetric electrodes for ion production may be positioned on the top substrate (electrode 502) and the bottom substrate (electrodes 504) of the glass wafers 308. The electrode alignment may be either directly above each other or offset to account for variations of the air flow.

Figure 6:
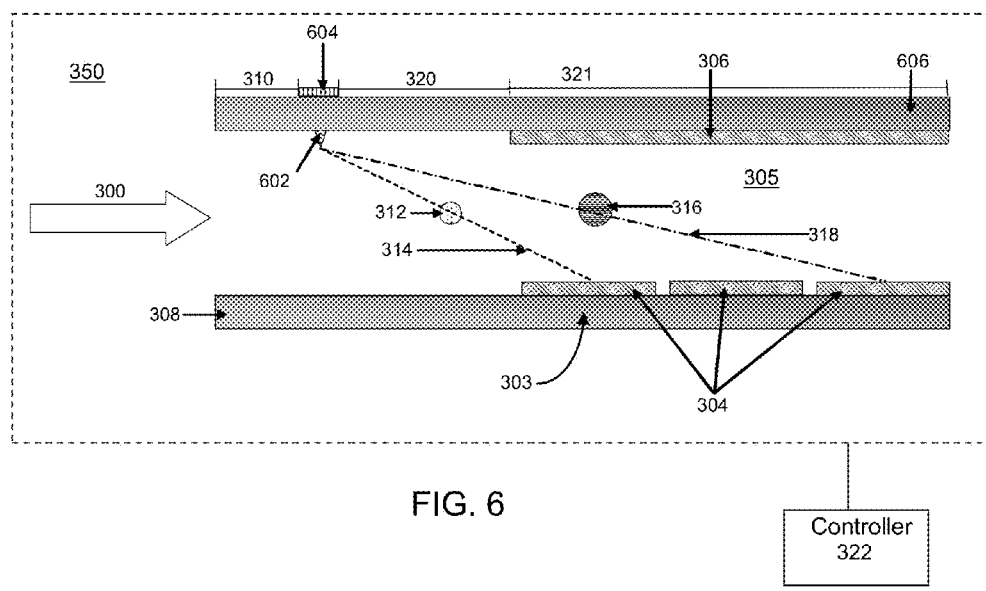
FIG. 6 is a schematic diagram depicting an IMS device with asymmetric ion production electrodes on the top substrate, and on either side of the dielectric material, in accordance with embodiments of the present invention.

FIG. 6 depicts another exemplary embodiment of the ion mobility spectrometer (IMS) 350. In the embodiment of FIG. 6, the plurality of asymmetric electrodes may include a first asymmetric electrode positioned on one of the plurality of substrates outside the measurement region, and a second asymmetric electrode positioned on the one of the plurality of substrates within the measurement region. For example, as depicted in FIG. 6, the asymmetric electrodes for ion production are positioned on the top substrate 606. In particular, an asymmetric electrode 604 may be positioned on top of the substrate 606 outside the flow channel or measurement region 305, with one or more asymmetric electrodes 602 being positioned inside the flow channel or measurement region. In such a configuration, the substrate 606 is a dielectric of suitable thickness for high voltage operation, and the applied voltage should be a time varying voltage of a suitable frequency to achieve electric discharge. The effect of applied frequency on dielectric barrier discharge is known to those of ordinary skill in the art. (See J. Phys IV France 7 (1997) C4-47-C4-66, Kogelschatz, Eliasson and Egli.)

Figure 7:
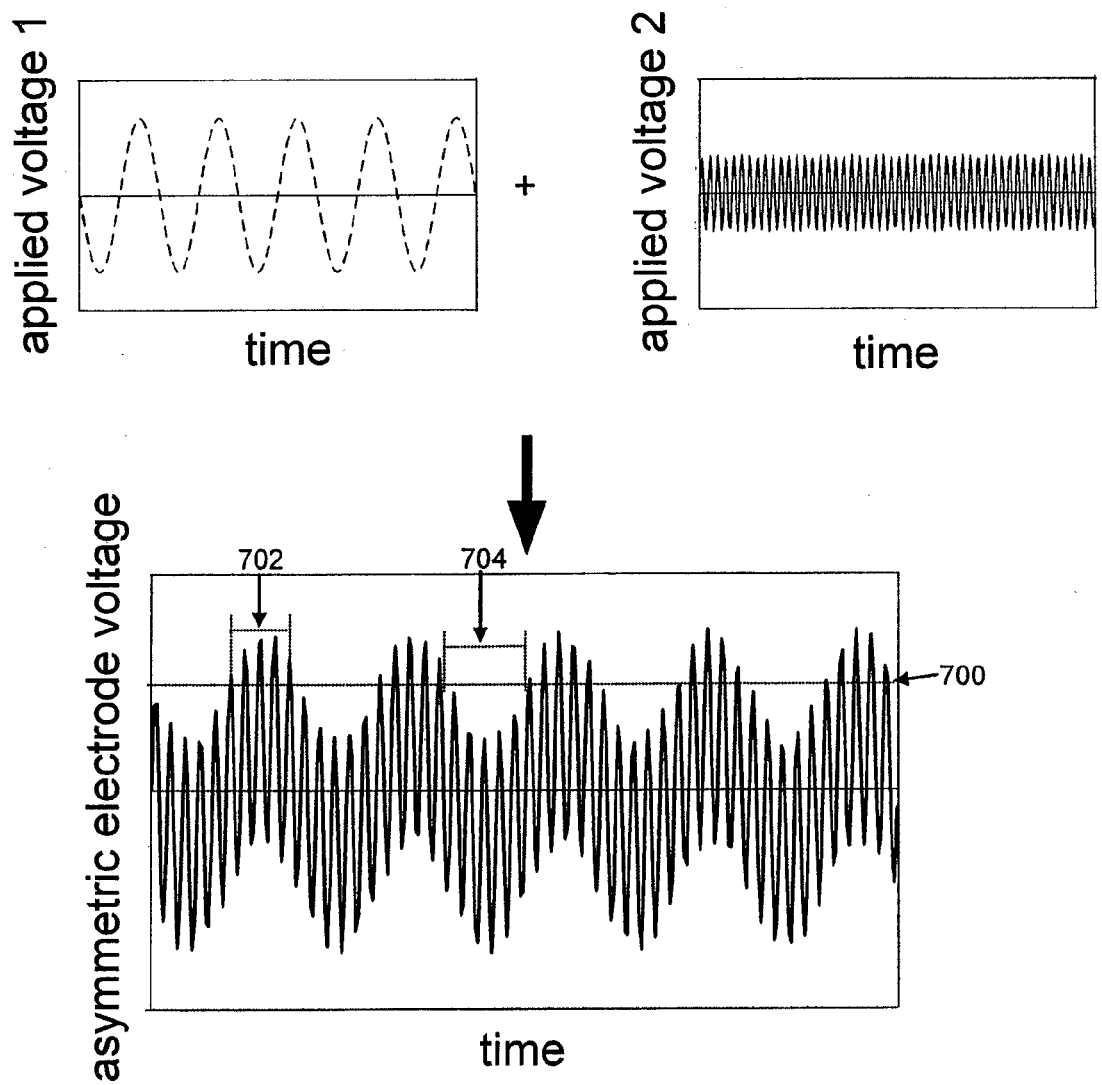
FIG. 7 is a graphical illustration of modulating applied high voltage frequencies to ensure ion production while maintaining a suitable separation of ion pulses in accordance with embodiments of the present invention.

In some circumstances, the frequency of the applied high voltage required to generate an electric discharge may be too high for use with the frequency analysis techniques at the detector electrodes. At too high frequencies, the ion pulses may be separated by a distance less than the distance an ion can diffuse in the available time. This could suppress the component of the measured current at the modulated frequency. FIG. 7 depicts a modulated voltage that may be applied to overcome such issues. As depicted in FIG. 7, the applied voltage may be modulated at two separate frequencies, a first frequency having a voltage above the ionization voltage for a time period during which ions are produced, and a second frequency to provide a separation period during which ions are not produced. As seen in FIG. 7, this modulation technique ensures there is a period in which the voltage is above the threshold ionization voltage 700, and consequently ions are produced during an ion production pulse 702 separated by a suitable ion pulse separation period 704.

Figure 8:
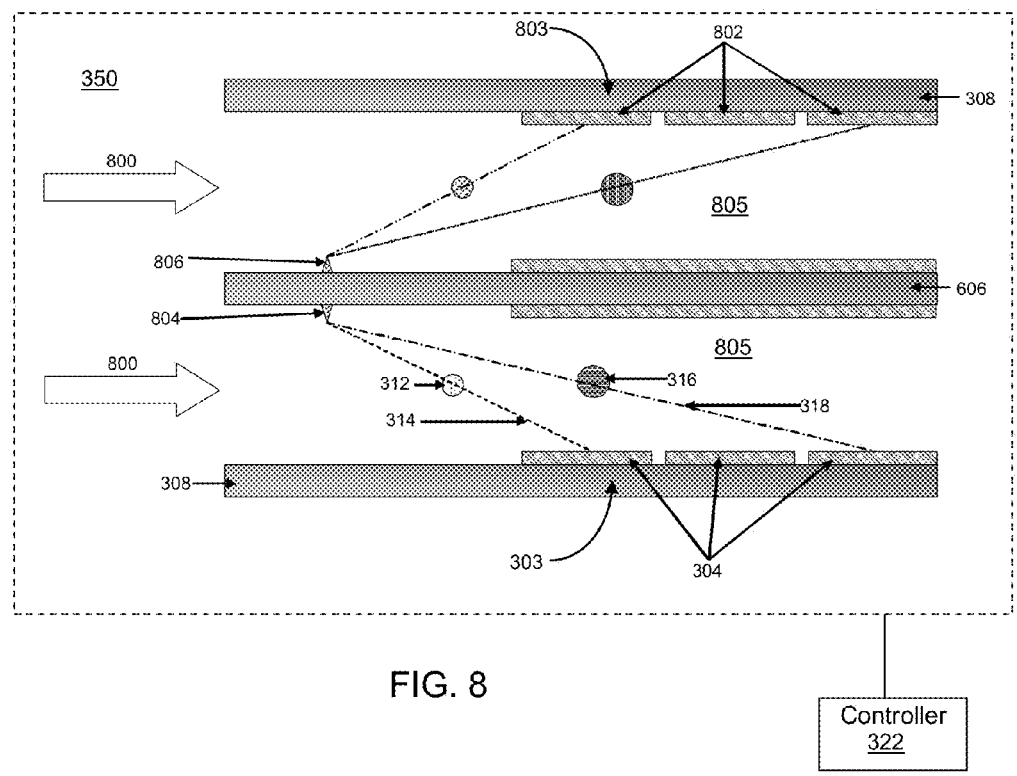
FIG. 8 is a schematic diagram depicting a multiple layered ion mobility spectrometer for simultaneous ion detection at different applied electric field strengths/polarities in accordance with embodiments of the present invention.

FIG. 8 depicts another exemplary embodiment of the ion mobility spectrometer (IMS) 350. In the embodiment of FIG. 8, at least three substrates are used to create a plurality of measurement regions, and two measurement regions 805 particularly in the embodiment of FIG. 8. The heights of the measurement regions are defined by the separation between the three substrates. For example, a first measurement region is provided between the upper substrate 308 and middle substrate 606, and a second measurement region is provided between the lower substrate 308 and middle substrate 606. The middle substrate 606 is a dielectric material, and an ionizing electrode including asymmetric electrodes for ion production 804 and 806 is positioned on opposite sides of the middle substrate 606. The dielectric substrate should be of a suitable thickness for high voltage operation, and the applied voltage should be time varying of a suitable frequency to achieve electric discharge. The application of a suitable time varying high voltage enables the production of ions in both measurement regions.

Both outer substrates 308 respectively may contain an array 303 and 803 of a plurality of detector electrodes 304 and 802 that are a suitable distance downstream from the asymmetric electrodes, similarly to the previous embodiments. As further depicted in FIG. 8, the sample air flow 800 is split so that laminar flow is obtained in both the first and second measurement regions prior to reaching the asymmetric electrodes 804 and 806. In the first measurement region, a positive electric field is applied to deflect negative ions onto the detector electrodes 802 of the detector electrode array 803. In the second measurement region, a negative electric field is applied to deflect positive ions onto the detector electrodes 304 of the detector electrode array 303. This allows the simultaneous detection of both positive and negative ions.

In another exemplary embodiment of the invention, the two detection regions may have applied electric fields of the same polarity but with different applied strengths or duty cycles in each region. This allows the simultaneous measurement of ion mobility under differing field strengths.

Figure 9:
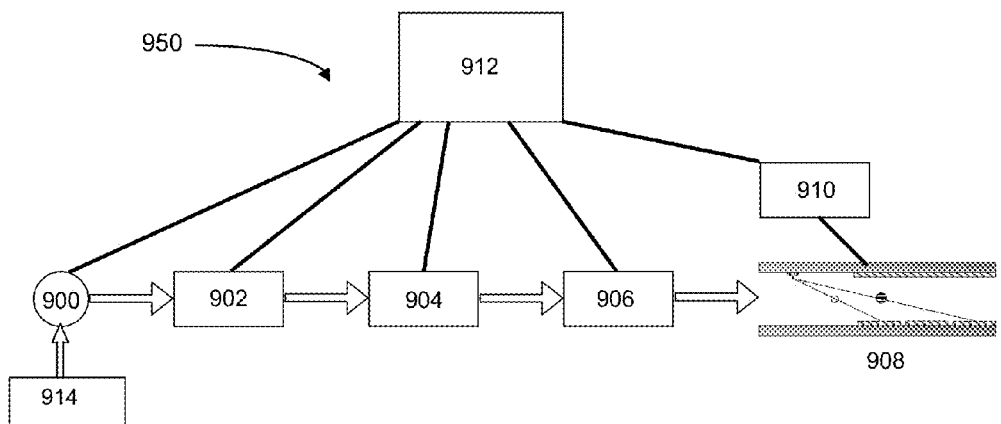
FIG. 9 is a schematic diagram depicting an IMS incorporated into a complete sample preparation and analysis system in accordance with embodiments of the present invention.

FIG. 9 depicts an exemplary gas analysis system 950 that may include an IMS device in accordance with the various embodiments described above. In a system such as that in FIG. 9, to ensure proper operation of the ion mobility spectrometer over prolonged periods, it is desirable for the sample gas to have undergone a preparation process prior to entering the IMS device. FIG. 9 depicts a system embodiment including an IMS device in which sample preparation and introduction is managed by a controlling microprocessor 912. The current at each electrode array element is amplified/measured using on-chip electronics incorporated into the electrode structures, and the data is processed and output using the controlling microprocessor. Exemplary components of the system of FIG. 9 may include the following:

The system may include an air pump 900 that pumps a gaseous sample into the system. The air pump 900 may be, for example, a mechanical pump, micro (membrane) pump or electrohydrodynamic flow (ionic wind) as are known in the art.

Next, the system may include a humidity controller 902 for adjusting the humidity of the sample air. The efficacy of electric discharge is affected by the atmospheric humidity; therefore, controlling the humidity helps provide stable ion production.

Next, the system may include an ion trap 904 for removing ionized species that initially may be present in the air sample. Removing any pre-existing ions in the air sample ensures that the only ions present in the sample air are created by the electric discharge, which minimizes background noise. Possible methods of employing the ion trap may include the application of a large electric field or ion exchange resins.

Next, the system may include a filter in the form of a particulate sizer or counter 906 that filters the air sample to remove airborne particulates. The filter 906 may also provide a mechanism for measuring the size and quantity of the particulates, which may be performed using a virtual impactor or particle counter.

In addition, the system may include a heating element 914 particularly suitable for heating of liquid or solid samples. In particular, solids and liquids may be heated to produce the gas sample that is analyzed in turn. Such heating enables the analysis of low volatility chemical species or improves the sensitivity by increasing the concentration of a species of interest.

Finally, as described above, the system may include detector electronics 910 including an IMS device 908 in accordance with one or more of the various embodiments described above. The IMS device may be combined with additional ionization mechanisms. For example, some chemical species may not be ionized sufficiently by electrical discharge methods, so alternative ionization techniques such as photoionization may be employed in conjunction with a described IMS device.

Although the invention has been shown and described with respect to a certain embodiment or embodiments, equivalent alterations and modifications may occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein exemplary embodiment or embodiments of the invention. In addition, while a particular feature of the invention may have been described above with respect to only one or more of several embodiments, such feature may be combined with one or more other features of the other embodiments, as may be desired and advantageous for any given or particular application.

INDUSTRIAL APPLICABILITY

This invention is relevant to any analytical technique sampling the chemical composition of a gaseous sample. These may be direct sampling of ambient air or involve sample preparation steps such as heating a solid or liquid sample to produce vapors of normally non-volatile chemicals. Possible industrial applications include air quality monitoring devices, demand control ventilation sensors and medical diagnostic breath analyzers, and to detect explosive and drug residues in security applications.

The invention claimed is:

1. An ion mobility spectrometer comprising:
a plurality of substrates defining a measurement region for receiving a singular laminar gas sample flow, wherein the measurement region comprises an ionization region that is continuous with a detection region;
an ionizing electrode for producing ions in the singular laminar gas sample within the ionization region by ionizing a portion of the singular laminar gas sample, wherein a non-ionized portion of the singular laminar gas sample acts as a carrier gas for the ionized portion of the singular laminar gas sample;
a field generating electrode for generating an electric field to deflect the ions in the gas sample;
a detection electrode array for detecting the deflected ions within the detection region; and
a controller configured to determine ion species based on the detection of ions by the detection electrode array.

2. The ion mobility spectrometer of claim 1, wherein the detection electrode array comprises a plurality of detection electrodes, and the controller is configured to differentiate ion species based on which ions are detected by which one of the detection electrodes.

3. The ion mobility spectrometer of claim 1, wherein the ionizing electrode comprises a plurality of asymmetric electrodes.

4. The ion mobility spectrometer of claim 3, wherein the plurality of asymmetric electrodes comprises a first asymmetric electrode positioned on a first of the plurality of substrates, and a second asymmetric electrode positioned on a second of the plurality of substrates.

5. The ion mobility spectrometer of claim 3, wherein the plurality of asymmetric electrodes comprises a first asymmetric electrode positioned on one of the plurality of substrates outside the measurement region, and a second asymmetric electrode positioned on the one of the plurality of substrates within the measurement region.

6. The ion mobility spectrometer of claim 1, wherein the field generating electrode produces an electric field that has a voltage polarity opposite to that of the ionizing electrode.

7. The ion mobility spectrometer of claim 1, wherein the measurement region comprises an ionization region in which the gas sample is ionized by the ionizing electrode, and a detection region containing the detection electrode array.

8. The ion mobility spectrometer of claim 1, comprising at least three substrates defining a plurality of measurement regions, wherein each measurement region receives a singular laminar gas sample flow.

9. The ion mobility spectrometer of claim 8, wherein a middle substrate of the three substrates includes a plurality of ionizing electrodes positioned on opposite sides of the middle substrate such that an ionizing electrode is positioned within each measurement region.

10. The ion mobility spectrometer of claim 9, wherein outer substrates of the three substrates each include a detection electrode array for detecting the deflected ions.

11. A method of determining ion species with an ion mobility spectrometer comprising the steps of:
providing a singular laminar gas sample flow;
defining a measurement region for receiving the singular laminar gas sample flow, wherein the measurement region comprises an ionization region that is continuous with a detection region;
ionizing the gas sample to produce ions in the singular laminar gas sample within the ionization region by ionizing a portion of the singular laminar gas sample, wherein a non-ionized portion of the singular laminar gas sample acts as a carrier gas for the ionized portion of the singular laminar gas sample;
generating an electric field within the detection region to deflect the ions in the gas sample;
detecting the deflected ions within the detection region with a detection electrode ray; and
determining ion species based on the detection of ions by the detection electrode array.

12. The method of determining ion species of claim 11, wherein the detection electrode array comprises a plurality of detection electrodes, and determining the ion species comprises differentiating ion species based which ions are detected by which one of the detection electrodes.

13. The method of determining ion species of claim 11, wherein ionizing the gas sample comprises applying a time varying voltage to the gas sample to generate a time dependent ion production.

14. The method of determining ion species of claim 13, wherein the applied ionizing voltage oscillates around an ionization threshold voltage at which chemical species in the air sample tend to ionize to generate an ion production switching on and off at a frequency of the oscillations.

15. The method of determining ion species of claim 14, wherein determining ion species further comprises performing a frequency analysis of the currents at the detector electrode array.

16. The method of determining ion species of claim 15, wherein the ionization voltage is modulated at two frequencies including a first frequency having a voltage above the ionization voltage during which ions are produce, and a second frequency to provide a separation period during which ions are not produced.

17. The method of determining ion species of claim 13, wherein ionizing the gas sample comprises applying a time varying voltage that is switched between a negative and positive polarity.

18. The method of determining ion species of claim 11, wherein generating an electric field within the detection electrode comprises applying a time varying electric field in the detection region.

19. A gas analysis system comprising:
a pump for pumping a singular laminar gas sample; and
the ion mobility spectrometer (IMS) of claim 1, wherein the IMS receives the gas sample from the pump.

20. The gas analysis system of claim 19, further comprising:
a humidity controller for controlling the humidity of the gas sample;
an ion trap for removing ions that are preexisting in the gas sample before the gas sample enters the ion mobility spectrometer; and
a filter for removing particulates from the gas sample.

21. The gas analysis system of claim 19, further comprising a heating element for heating a solid or liquid material to produce the gas sample.

* * * * *